United States Patent
Baxter et al.

(10) Patent No.: US 8,199,319 B2
(45) Date of Patent: Jun. 12, 2012

(54) FIBER PROPERTY MEASUREMENT

(75) Inventors: Preston S. Baxter, Friendsville, TN (US); Youe-Tsyr Chu, Knoxville, TN (US); Hossein M. Ghorashi, Knoxville, TN (US); Michael E. Galyon, Knoxville, TN (US)

(73) Assignee: Uster Technologies AG, Uster (CH)

( * ) Notice: Subject to any disclaimer, the term of this patent is extended or adjusted under 35 U.S.C. 154(b) by 226 days.

(21) Appl. No.: 12/493,334

(22) Filed: Jun. 29, 2009

(65) Prior Publication Data

US 2010/0328650 A1 Dec. 30, 2010

(51) Int. Cl.
G01N 21/00 (2006.01)
G01J 3/46 (2006.01)

(52) U.S. Cl. ........................ 356/73.1; 356/402; 356/407

(58) Field of Classification Search .... 356/238.1–238.3, 356/402–406, 429–430
See application file for complete search history.

(56) References Cited

U.S. PATENT DOCUMENTS

| | | | |
|---|---|---|---|
| 5,087,120 A | 2/1992 | Anthony et al. | |
| 5,125,279 A | 6/1992 | Anthony et al. | |
| 5,321,496 A | 6/1994 | Shofner et al. | |
| 5,539,515 A * | 7/1996 | Shofner et al. | 356/238.3 |
| 5,639,955 A * | 6/1997 | Anthony | 73/1.01 |
| 5,753,906 A * | 5/1998 | Gennetten | 250/226 |
| 5,805,452 A | 9/1998 | Anthony et al. | |
| 5,943,907 A | 8/1999 | Ghorashi et al. | |
| 6,040,905 A | 3/2000 | Cheng et al. | |
| 6,052,182 A | 4/2000 | Irick, Sr. et al. | |
| 6,098,454 A | 8/2000 | Ghorashi et al. | |
| 6,112,131 A | 8/2000 | Ghorashi et al. | |
| 6,314,806 B1 | 11/2001 | Ghorashi et al. | |
| 6,567,538 B1 | 5/2003 | Pelletier | |
| 6,735,327 B1 * | 5/2004 | Shofner et al. | 382/111 |
| 6,870,897 B2 | 3/2005 | Sari-Sarraf et al. | |
| 7,333,203 B2 * | 2/2008 | Ott | 356/430 |
| 2003/0059090 A1 | 3/2003 | Zhang et al. | |

* cited by examiner

Primary Examiner — Tarifur Chowdhury
Assistant Examiner — Tara S Pajoohi Gomez
(74) Attorney, Agent, or Firm — Luedeka Neely Group, P.C.

(57) ABSTRACT

A fiber instrument for measuring properties of a fiber sample, the fiber instrument having a surface for receiving the fiber sample, a hand for pressing the fiber sample against the surface, an illumination source for selectively illuminating the fiber sample with more than one peak wavelength, where each of the peak wavelengths is independently controllable as to an applied intensity of the peak wavelength, a sensor for capturing images of the fiber sample while it is illuminated, and a controller for controlling at least the sensor and the illumination source. By providing multiple peak wavelengths of illumination that are each independently controllable as to illumination intensity, the fiber instrument as described herein is better able to detect both foreign material within the fiber sample, and color gradations of the fiber sample.

19 Claims, 1 Drawing Sheet

FIBER PROPERTY MEASUREMENT

FIELD

This invention relates to the field of fiber quality measurements. More particularly, this invention relates to detecting non-fiber entities (such as trash) that is mixed in with fibers, such as cotton fibers.

BACKGROUND

Natural and man-made fibers are routinely assessed for a variety of different properties, so as to grade the fiber samples. These properties include things such as fiber length, strength, color, moisture content, straightness, fineness, and non-fiber content. For example, measuring the properties of cotton fiber so as to provide a grade for the quality of the cotton is an important step in obtaining the value of the fibers as well as its impact on the quality of the cotton yarn and fabric. Originally, the classification of fiber samples relied upon the senses of human classers who would visually observe the fiber samples and assign them a grade accordingly. However, the use of human classers tends to be variable and heavily dependent upon the skill of the individual.

Electronic instruments have started to be used to grade fibers, such as cotton. However, electronic instruments tend to have problems detecting the fine variations in the cotton properties that a human classer is able to detect.

It is desired that continual improvements be made in such instruments, to make them, for example, more uniform in the detection of the fiber properties, able to measure more fiber samples in less time, able to more easily, reliably, and repeatably detect and identify an expanded set of fiber and non-fiber characteristics, and to increase the reliability and longevity of such equipment.

SUMMARY

The above and other needs are met at least in part by a fiber instrument for measuring properties of a fiber sample, the fiber instrument having a surface for receiving the fiber sample, a hand for pressing the fiber sample against the surface, an illumination source for selectively illuminating the fiber sample with more than one peak wavelength, where each of the peak wavelengths is independently controllable as to an applied intensity of the peak wavelength, a sensor for capturing images of the fiber sample while it is illuminated, and a controller for controlling at least the sensor and the illumination source.

By providing multiple peak wavelengths of illumination that are each independently controllable as to illumination intensity, the fiber instrument as described herein is better able to detect both foreign material within the fiber sample, and color gradations of the fiber sample.

In various embodiments according to this aspect of the invention, the surface is at least one of glass, quartz, and sapphire. In some embodiments the hand is multiple hands that are each individually controllable as to a degree of pressure asserted on the fiber sample against the surface. In some embodiments the illumination source is multiple illumination sources. In some embodiments the peak wavelengths of illumination correspond to one each of yellow light, red light, green light, and blue light. In some embodiments the sensor is at least one of a camera and a charge coupled device. In some embodiments the controller is a personal computer. In some embodiments the fiber sample is cotton.

According to another aspect of the invention there is described a fiber instrument for measuring properties of a fiber sample, have a surface for receiving the fiber sample, more than one hand for pressing the cotton sample against the surface with a uniform pressure, an illumination source for illuminating the fiber sample, a sensor for capturing images of the fiber sample while it is illuminated, and a controller for controlling the sensor and the illumination source.

According to yet another aspect of the invention there is described a method for measuring properties of a fiber sample, by receiving the fiber sample against a surface, pressing the fiber sample against the surface, illuminating the fiber sample with more than one different peak wavelengths of illumination, separately controlling the illumination intensity of the more than one peak wavelengths of illumination, and capturing images of the fiber sample while it is illuminated.

In various embodiments according to this aspect of the invention, the step of illuminating the fiber sample includes illuminating the fiber sample with a first illumination of a first of the different peak wavelengths of illumination at a first illumination intensity, capturing a first image of the fiber sample during the first illumination, halting the first illumination, illuminating the fiber sample with a second illumination of a second of the different peak wavelengths of illumination at a second illumination intensity that is different from the first illumination intensity, capturing a second image of the fiber sample during the second illumination, and halting the second illumination. In some embodiments the fiber sample is pressed against the surface using multiple points of contact so as to balance an exerted pressure across the fiber sample.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
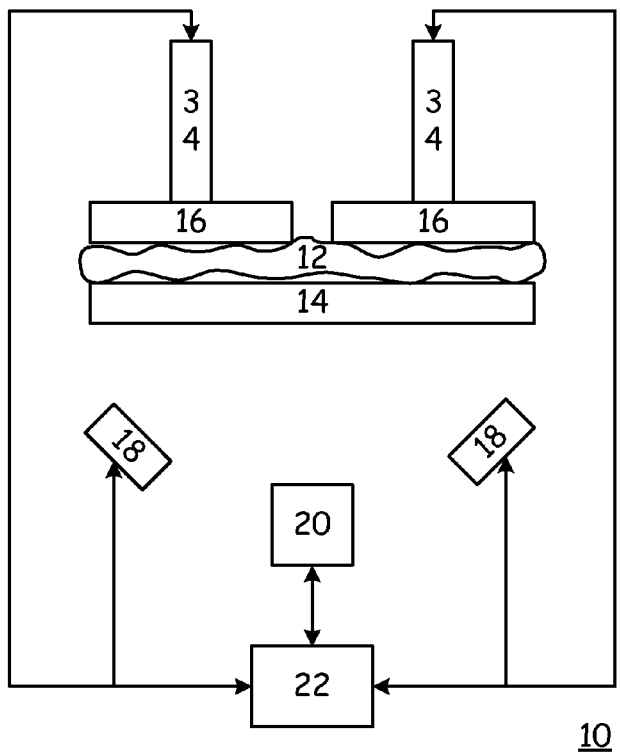
FIG. 1 is a functional block diagram of a fiber instrument according to an embodiment of the present invention.

With reference now to the figures, there are described various embodiments of a fiber instrument. FIG. 1 depicts a function block diagram of a fiber instrument 10 according to an embodiment of the present invention, which is operable for taking measurements on a fiber sample 12, such as an amount of cotton. The basic elements of the fiber instrument 10 are a surface 14 on which the fiber sample 12 is disposed, at least one hand 16 that presses the fiber sample 12 against the surface 14, at least one compressor 34 that pushes the hands 16 against the fiber sample 12, at least one illumination source 18 that illuminates the fiber sample 12 from beneath the surface 14, at least one sensor 20 that captures measurements of the fiber sample 12, and a controller 22 in communication with the various elements of the fiber instrument 10, which controller 22 is operable to send commands to and receive information from the various elements, so as to control the fiber instrument 10 in a desired manner, as described in a few example embodiments below.

The fiber instrument 10 in some embodiments is extremely large, so as to be able to handle very large fiber samples 12, while in other embodiments the fiber instrument 10 is quite small, so as to be conveniently portable. One of the elements that tends to govern the overall size of the fiber instrument 10 is the surface 14. In the larger embodiments of the fiber instrument 10, the surface 14 is as large as several square feet, while in the smaller embodiments the surface 14 is as small as less than nine square inches. Thus, different sizes of the fiber instrument 10 are able to accommodate smaller or larger sizes of the fiber sample 12, and are intended for either relatively permanent installation or for portable use.

The fiber sample 12 can take various forms. In one embodiment, the fiber sample 12 is cotton that is placed manually upon the surface 14. In other embodiments, the fiber sample 12 is a fiber that is flowing through an air duct system, such as cotton through a cotton gin or mill, that is automatically captured and placed against the surface 14. In other embodiments the fiber sample 12 is wool or a man-made fiber.

The surface 14 against which the fiber sample 12 is placed allows the fiber sample 12 to be illuminated and viewed from the opposite side of the surface 14, which in the embodiment as depicted in FIG. 1 is from below the surface 14. However, it is appreciated that in other embodiments, the surface 14 can be disposed in other orientations, such as upside down or sideways from that as depicted in FIG. 1. To permit the illumination and viewing of the fiber sample 12 through the surface 14, the surface 14 either has openings in it—such as a mesh or weave, or is a sheet of a material that is at least partially transmissive to the desired wavelengths of radiation. In this manner, illumination is able to pass through the surface 14 and reflect off of the fiber sample 12, passing back through the surface 14. In some embodiments, the surface 14 is substantially clear and virtually completely transmissive to illumination, at least to an illumination within the radiation peaks of interest, as described in more detail below. For example, in some embodiments the surface 14 is formed of at least one of wire mesh, glass, quartz, sapphire, or some other such material. In most embodiments the surface 14 is substantially planar. In some embodiments the surface 14 has a square shape in the top plan view, but in other embodiments it can have other shapes as desired, such as circular.

At least one hand 16 presses the fiber sample 12 against the surface 14. The number of hands 16 used can be based on one or more criterion, such as the size of the surface 14. For example, a larger surface 14 might well use a larger number of individual hands 16 to press the fiber sample 12 against the surface 14, so as to even out the pressure that is applied across a non-uniform fiber sample 12. To explain more, a larger fiber sample 12 might have some areas where more fiber is disposed and other areas where less fiber is disposed, as is the nature of samples of fibers, which tend to be wadded in some places and thinned in others. By providing more hands 16 on such relatively larger surfaces 14, each individual hand 16 can apply a similar amount of pressure to the hills and dales (so to speak) in the fiber sample 12, whereas a single hand 16 would tend to apply all of the pressure to the hills and none of the pressure to the dales.

In some embodiments, a sufficient number of hands 16 is provided, or one or more hands 16 of a given size are provided, such that the surface area of the hands 16 substantially matches the surface area of the surface 14. In other embodiments, the combined surface area of the hands 16 is either greater than or less than the surface area of the surface 14. For example, in some embodiments the measurements taken by the fiber instrument 10 might be improved by having the fiber sample 12 compressed beyond the circumferential edges of the surface 14, while in other embodiments the measurements taken by the fiber instrument 10 might be improved by the fiber sample 12 remaining uncompressed just within the circumferential edges of the surface 14.

Figure 4:
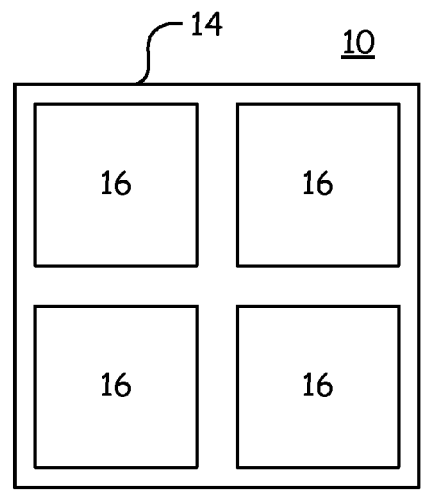
FIG. 4 depicts hands on a surface according to an embodiment of the present invention.

With reference now to FIG. 4, there is depicted a top plan view of the fiber instrument 10, depicting an embodiment where four hands 16 cover substantially all of the surface 14. As described above, other embodiments are also contemplated.

Referring back again to FIG. 1, the compressors 34 press the hands 16 against the fiber sample 12, thereby pressing the fiber sample 12 against the surface 14. Each hand 16 has at least one compressor 34 associated with it. The compressors 34 in some embodiments are linear cylinders, such as pneumatically or hydraulically driven cylinders. In other embodiments the compressors 34 take other forms, such as screws or rack and pinion devices. The compressors 34 can move the hands 16 in a linear manner, or can rotate the hands 16 down onto the fiber sample 12.

Figure 3:
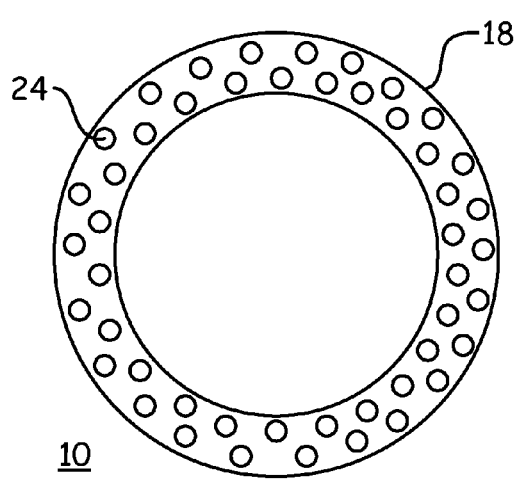
FIG. 3 depicts an illumination source according to a second embodiment of the present invention.

The illumination sources 18 illuminate the fiber sample 12, such as during the acquisition of a measurement. In some embodiments the illumination sources 18 illuminate the fiber sample 12 at all times—or in other words, are substantially continuously lit. In other embodiments the illumination sources 18 illuminate the fiber sample 12 only when a measurement is captured from the fiber sample 12. At least one illumination source 18 is used to illuminate the fiber sample 12. In some embodiments the illumination sources 18 are balanced around the underside of the surface 14, so as to provide a relatively uniform illumination of all portions of the fiber sample 12 that are presented to the surface 14. FIG. 3 depicts an illumination source 18 fabricated in the form of a ring, to provide a uniform illumination of the fiber sample 12.

Figure 2:
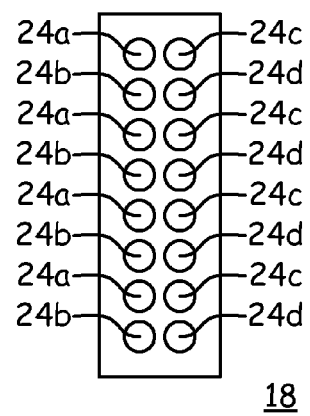
FIG. 2 depicts an illumination source according to a first embodiment of the present invention.

With reference now to FIG. 2, there is depicted a more detailed view of an illumination source 18. The illumination source 18 in the embodiment as depicted includes a plurality of lamps 24. The illumination source 18 selectively provides at least two peak wavelengths, where each of the peak wavelengths is independently controllable as to the applied intensity of the peak wavelength. The selectable peak wavelengths can be applied either one at a time or concurrently. Some of the lamps 24, such as 24a, provide an illumination with a first peak wavelength, and others of the lamps 24, such as 24b, provide an illumination with a second peak wavelength. In one embodiment, four different peak wavelengths are provided, created by lamps 24a, 24b, 24c, and 24d. In other embodiments, more than four peak wavelengths are provided, by providing more than four different types of lamps 24, or by providing lamps 24 that are capable of emitting more than one peak wavelength, either simultaneously or at different times, within each lamp.

For example, the peak wavelengths could generally conform to radiation corresponding to yellow, red, blue, and green visible light. Other peak wavelengths could be used in other embodiments. In other embodiments the peak wavelengths overlap one another to some degree. In some embodiments these different peak wavelengths are provided by different lamps 24, as described above. In other embodiments these different peak wavelengths are provided by the same lamps 24, which are operated in a manner so as to produce these different peak wavelengths at different times, according to the manner in which the lamps 24 are operated.

The lamps 24 are configured such that the intensity of a given peak wavelength is individually and independently adjustable from the intensity of a different peak wavelength. Thus, an illumination of the fiber sample 12 in a first peak wavelength can be performed with a first intensity, and a second illumination of the fiber sample 12 in a second peak wavelength can be performed with a second intensity, where the first intensity and the second intensity are not the same intensity, and the first intensity and the second intensity are individually and independently adjusted and controlled. However, the first illumination and the second illumination can be either simultaneously performed or serially performed, as desired.

In some embodiments, the fiber sample 12 is illuminated with more than one of the different peak wavelengths simultaneously, and one or more measurements are collected from the fiber sample 12 during the simultaneous illumination. In other embodiments, the fiber sample 12 is illuminated with just one of the different peak wavelengths at a time, and separate and independent measurements are collected from the fiber sample 12 during the separate illuminations. In some embodiments multiple sets of the different lamps 24a-d are provided within a single illumination source 18.

With reference once again to FIG. 1, the sensor 20 is operable to capture measurements of the fiber sample 12, such as when the fiber sample 12 is illuminated by the illumination source 18. In some embodiments the sensor 20 is an image capture device, such as a camera with film or a charge coupled device, for example. In some embodiments the sensor 20 has a field of view that is sufficient to capture a measurement of the entire surface area of the fiber sample 12 as it is pressed against the surface 14. In some embodiments the sensor 20 has a field of view that can be reduced to smaller surface areas while using the same number of pixels in the sensor 20 (thereby increasing the resolution) such as with a zoom function, and which can be moved from one portion of the surface area of the fiber sample 12 to another.

The operation of the fiber instrument 10 is under the control of the controller 22. The controller 22 is preferably programmable, such as by an operator through a means such as a keyboard or touch screen, or which can receive programming remotely, such as through a network connection. The controller 22 in some embodiments not only controls the operation of the various elements of fiber instrument 10 such that they act in concert one with another, but also receives information back from the various elements of the fiber instrument 10, such that the controller 22 is aware of the condition and operation of the various elements. For example, the controller 22 in some embodiments receives pressure information back from either the surface 14 or the hands 16 or the compressors 34. In some embodiments the controller 22 receives a data stream back from the sensor 20. The controller 22 of some embodiments can present—such as on a display device like a screen—information in regard to the operation of the fiber instrument 10, and the measurement information that is captured by the sensor 20. In some embodiments the controller 22 is a personal computer, and in other embodiments the controller 22 is an embedded controller.

The fiber instrument 10 is operated, in one embodiment, by loading a fiber sample 12 onto the surface 14, and pressing the fiber sample 12 against the surface 14 by pressing the hands 16 onto the fiber sample 12 with the compressors 34. When a desired amount of pressure is exerted against the fiber sample 12, the lamps 24 of the illuminators 18 are energized, such that the fiber sample 12 is illuminated with one of the peak wavelengths of radiation at a desired intensity. The sensor 20 then captures an image of the fiber sample 12, which is stored, such as with the controller 22. The fiber sample 12 is then illuminated with a different one of the peak wavelengths of radiation, again at an intensity that is desired for that peak wavelength, which can be a different intensity. Once again, the sensor 20 captures an image of the fiber sample 12, which is stored in the controller 22. This process of illuminating the fiber sample 12 with one of the different peak wavelengths, and at an individually and independently controlled intensity, is repeated as desired, with an image captured by the sensor 20 for each illumination cycle.

In some embodiments, the fiber sample 12 is illuminated with more than one of the peak wavelengths at a given time, and an image is captured. In some embodiments, the images that are captured during each independent illumination cycle are mathematically combined into a single composite image, such as by the controller 22. In other embodiments the different images that are captured during each independent illumination cycle are analyzed independently.

Once the desired images are captured by the sensor 20 and stored by the controller 22, the controller 22 or some other processing device then analyzes the one or more images to determine certain properties of the fiber sample 12. For example, by analyzing images that are captured while illuminating the fiber sample 12 in different peak wavelengths of radiation, where the intensity of those peak wavelengths is individually and independently controllable, it has been determined that it is much easier to detect foreign material that is mixed in with the fiber sample 12, where "foreign material" means material that is not formed of the same material of which the fibers in the fiber sample 12 are formed.

For example, in cotton processing, foreign material is typically referred to as trash, and contains material such as bark, leaves, sticks, husks, and other organic materials and inorganic materials that can be picked up along with the cotton fibers. The images that are captured of cotton samples 12 using different wavelengths at different intensities make it much easier to discriminate the trash from the cotton fiber and make grading measurements of the cotton sample 12.

Thus, a fiber instrument 10 as describe herein can be used to perform cotton grading measurements, because of its enhanced ability to take measurements, such as trash measurements or color measurements.

The fiber instrument 10 can be operated in some embodiments with different fiber samples 12 loaded simultaneously on the surface 14, and the sensor 20 can be directed to capture individual images of those different samples 12. For example, a different fiber sample 12 can be loaded under different ones of the hands 16. In some embodiments, the sensor 20 captures separate images of a common fiber sample 12 that is placed against the surface 14, where the separate images are associated with different quadrants or other divisions of the surface 14, and which different portions are either illuminated with a different wavelength, or at a different intensity, or compressed with a different pressure. All such permutations of operating parameters can be programmed through the controller 22.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A fiber instrument for measuring properties of a fiber sample, comprising:
   a surface for receiving the fiber sample,
   a hand for pressing the fiber sample against the surface,
   an illumination source for selectively illuminating the fiber sample with a plurality of different peak wavelengths, the illumination source having lamps, wherein a given one of the lamps provides illumination at only a given one of the peak wavelengths, wherein the lamps are selectively controllable to illuminate the fiber sample at a variable desired applied intensity of a desired selection of the peak wavelengths,
   a sensor for capturing images of the fiber sample while it is illuminated, and
   a controller for controlling at least the sensor and the illumination source.

2. The fiber instrument of claim 1, wherein the surface comprises at least one of glass, quartz, and sapphire.

3. The fiber instrument of claim 1, wherein the hand comprises multiple hands that are each individually controllable as to a degree of pressure asserted on the fiber sample against the surface.

4. The fiber instrument of claim 1, wherein the illumination source comprises multiple illumination sources.

5. The fiber instrument of claim 1, wherein the peak wavelengths correspond to one each of yellow light, red light, green light, and blue light.

6. The fiber instrument of claim 1, wherein the sensor comprises at least one of a camera and a charge coupled device.

7. The fiber instrument of claim 1, wherein the controller comprises a personal computer.

8. The fiber instrument of claim 1, wherein the fiber sample comprises cotton.

9. A fiber instrument for measuring properties of a fiber sample, comprising:
   a surface for receiving the fiber sample,
   more than one hand for pressing the fiber sample against the surface with a uniform pressure,
   an illumination source for selectively illuminating the fiber sample with a plurality of different peak wavelengths, the illumination source having lamps, wherein a given one of the lamps provides illumination at only a given one of the peak wavelengths, wherein the lamps are selectively controllable to illuminate the fiber sample at a variable desired applied intensity of a desired selection of the peak wavelengths,
   a sensor for capturing images of the fiber sample while it is illuminated, and
   a controller for controlling the sensor and the illumination source.

10. The fiber instrument of claim 9, wherein the surface comprises at least one of glass, quartz, and sapphire.

11. The fiber instrument of claim 9, wherein the hands are each individually controllable as to a degree of pressure asserted on the fiber sample against the surface.

12. The fiber instrument of claim 9, wherein the illumination source comprises multiple illumination sources.

13. The fiber instrument of claim 9, wherein the illumination source provides peak wavelengths of illumination corresponding to one each of yellow light, red light, green light, and blue light.

14. The fiber instrument of claim 9, wherein the sensor comprises at least one of a camera and a charge coupled device.

15. The fiber instrument of claim 9, wherein the controller comprises a personal computer.

16. The fiber instrument of claim 9, wherein the fiber sample comprises cotton.

17. A method for measuring properties of a fiber sample, the method comprising the steps of:
   receiving the fiber sample against a surface,
   pressing the fiber sample against the surface,
   illuminating the fiber sample with more than one lamps providing a plurality of different peak wavelengths of illumination,
   selectively controlling the lamps to illuminate the fiber sample at a variable desired applied intensity of a desired selection of the peak wavelengths, and
   capturing images of the fiber sample while it is illuminated.

18. The method of claim 17, wherein the step of illuminating the fiber sample further comprises:
   illuminating the fiber sample with a first illumination of a first of the different peak wavelengths of illumination at a first illumination intensity,
   capturing a first image of the fiber sample during the first illumination,
   halting the first illumination,
   illuminating the fiber sample with a second illumination of a second of the different peak wavelengths of illumination at a second illumination intensity that is different from the first illumination intensity,
   capturing a second image of the fiber sample during the second illumination, and
   halting the second illumination.

19. The method of claim 17, wherein the fiber sample is pressed against the surface using multiple points of contact so as to balance an exerted pressure across the fiber sample.

* * * * *